United States Patent [19]

Caton et al.

[11] 3,935,261

[45] Jan. 27, 1976

[54] CYCLOPENTANE DERIVATIVES

[75] Inventors: Michael Peter Lear Caton, Upminster; Edward Charles John Coffee, London; Gordon Leonard Watkins, Dagenham, all of England

[73] Assignee: May & Baker Limited, England

[22] Filed: Sept. 3, 1974

[21] Appl. No.: 502,976

Related U.S. Application Data

[60] Division of Ser. No. 343,460, March 21, 1973, Pat. No. 3,884,942, which is a continuation-in-part of Ser. No. 108,981, Jan. 22, 1971, abandoned.

[30] Foreign Application Priority Data

Jan. 23, 1970 United Kingdom.............. 3494/70
Mar. 2, 1973 United Kingdom............ 10402/73

[52] U.S. Cl. ........ 260/557 R; 260/345.8; 260/345.9; 260/464; 260/468 D; 260/469; 260/488 R; 260/501.1; 260/514 D; 260/544 R; 260/557 H; 260/586 R; 260/598; 424/298; 424/316; 424/317; 424/320
[51] Int. Cl.² ............... C07C 102/00; C07C 103/37
[58] Field of Search .................... 260/557 R, 557 H

[56] References Cited
UNITED STATES PATENTS

| 3,432,541 | 3/1969 | Bagli et al. .................... 260/468 D |
| 3,455,992 | 7/1969 | Bagli et al. .................... 260/468 D |
| 3,501,525 | 3/1970 | Lapidus et al. ............. 260/468 D X |
| 3,504,019 | 3/1970 | Lapidus et al. ............. 260/468 D X |
| 3,505,386 | 4/1970 | Babcock et al. ................ 260/468 D |
| 3,505,387 | 4/1970 | Beal et al. ...................... 260/468 D |
| 3,751,463 | 8/1973 | Caton et al. ................... 260/557 R |
| 3,880,883 | 4/1975 | Caton et al. ................ 260/557 R X |

*Primary Examiner*—Robert V. Hines
*Assistant Examiner*—Thomas A. Waltz
*Attorney, Agent, or Firm*—Stevens, Davis, Miller & Mosher

[57] ABSTRACT

Cyclopentane derivatives of the prostaglandin type of the formula:

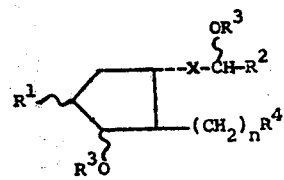

(wherein $R^1$ represents hydrogen or lower alkyl, $R^2$ represents alkyl of 1 to 10 carbon atoms, the symbols $R^3$ are the same and represent hydrogen, lower alkyl, lower alkenyl, phenyl(lower)alkyl or lower alkanoyl, $R^4$ represents a carboxy or alkoxycarbonyl group, or an amido group unsubstituted or substituted on the nitrogen atom, X represents vinylene, ethylene, epoxyethylene or cyclopropylene, and $n$ represents an integer of 5 to 8), which possess pharmacological properties in particular the production of hypotension, bronchodilation, inhibition of gastric acid secretion and stimulation of uterine contraction are prepared by a new six-stage process involving initially the reaction of an enamine of a cyclopentanone with an aldehyde to form a 2-hydroxyalkyl-2-cyclopenten-1-one, reacting the cyclopentenone with a source of hydrogen cyanide to form a hydroxyalkyl-3-oxocyclopentanecarbonitrile, reducing the carbonitrile to a 3-hydroxy-2-hydroxyalkyl-cyclopentanecarbaldehyde, reacting the carbaldehyde with an alkanoylmethylenephosphorane to convert the formyl group to ———CH=CH —CO—$R^2$, oxidising the terminal hydroxymethyl group in the 2-position substituent to carboxy and the ring hydroxy group to oxo, and reducing the two oxo groups in the resulting cyclopentanonealkanoic acid to yield a 2-hydroxy-5-(3-hydroxyalkenyl)cyclopentylalkanoic acid, and optionally converting the product into another compound of the foregoing formula.

3 Claims, No Drawings

CYCLOPENTANE DERIVATIVES

This is a division of application Ser. No. 343,460, filed Mar. 21, 1973, now U.S. Pat. No. 3,884,942, which in turn is a continuation-in-part of application Ser. No. 108,981, filed Jan. 22, 1971, and now abandoned. This invention relates to a new process for the preparation of therapeutically useful cyclopentane derivatives, and to intermediates used in the process.

An object of the present invention is to provide a new process for the preparation of cyclopentane derivatives of the general formula:

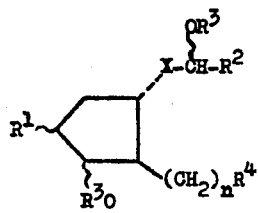

[wherein $R^1$ represents a hydrogen atom or a lower alkyl group, $R^2$ represents a straight- or branched-chain alkyl group containing 1 to 10 (preferably 4 to 9) carbon atoms — when branched it is preferred that the branching occurs at the carbon atom attached to the

grouping — the symbols $R^3$ represent identical groups selected from hydrogen atoms, lower alkyl, lower alkenyl, phenyl(lower)alkyl and lower alkanoyl groups, $R^4$ represents a carboxy group or a group of the formula:

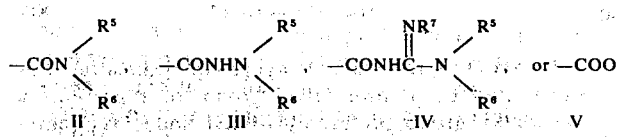

(wherein $R^5$, $R^6$ and $R^7$ are the same or different and each represents a hydrogen atom or a lower alkyl group, and $R^8$ represents a lower alkyl group), X represents a vinylene, ethylene, epoxyethylene or cyclopropylene group, n represents an integer from 5 to 8 inclusive, preferably 5, 6 or 7] and, when $R^4$ represents a carboxy group, non-toxic salts thereof.

In this specification, it is to be understood that reference to "lower alkyl groups" indicates alkyl groups containing from 1 to 4 carbon atoms, reference to "lower alkenyl groups" indicates alkenyl groups containing from 2 to 4 carbon atoms, and reference to "lower alkanoyl groups" indicates alkanoyl groups containing from 2 to 5 carbon atoms, such groups having straight- or branched chains.

It is known from U.S. Pat. No. 3,432,541 granted on 11th March 1969 to J. F. Bagli and T. Bogri that the compound of the foregoing formula wherein symbols $R^1$ and $R^3$ all represent hydrogen atoms, $R^2$ represents the pentyl group, $R^4$ represents the carboxy group, X represents the vinylene group and n represents 6, i.e. the compound 7-[2-hydroxy-5-(3-hydroxy-1-octenyl)-cyclopentyl]heptanoic acid (which may alternatively be named as 9,15-dihydroxyprost-13-enoic acid) possesses valuable hypotensive and anti-hypertensive properties. In the said U.S. patent there is described a process for the preparation of that particular compound which, as described, involves thirteen reaction steps commencing with two types of basic starting materials which are readily accessible, i.e. lower alkyl esters of ω-halogenated-haptanoic acid such as ethyl ω-bromoheptanoate, and alkali metal salts of lower alkyl esters of cyclopentanone-2-carboxylic acid such as the potassium salt of ethyl cyclopentanone-2-carboxylate, and going through — as the product of the seventh step — the intermediate 2-(6-carbomethoxyhexyl)cyclopentan-1-one-3-carboxylic acid chloride.

In U.S. Pat. No. 3,455,992 granted on 15th July 1969 to J. F. Bagli and T. Bogri there is described an alternative sequence of reaction steps for the preparation of the same heptanoic acid compound, and its homologues, for the latter stages of the process described in U.S. Pat. No. 3,432,541, i.e. from 2-(6-carbomethoxyhexyl)cyclopentan-1-one-3-carboxylic acid, but even this modification of the process still involves a total of eleven or twelve reaction steps from the same two types of basic readily accessible starting materials.

As a result of research and experimentation there has been discovered a new and improved process, which when applied to the production of 7-[2-hydroxy-5-(3-hydroxy-1-octenyl)cyclopentyl]heptanoic acid and related compounds, possesses advantages over the processes disclosed in U.S. Pat. Nos. 3,432,541 and 3,455,992 in that it involves a lesser number of reaction steps from starting materials, which are readily available commercially or easily accessible by known methods.

The new process of the present invention employs as basic starting materials onamines of cyclopentanones of the general formula:

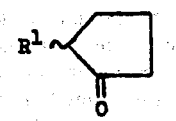

(wherein $R^1$ is as hereinbefore defined) and aldehydes of the general formula:

$$R^9O(CH_2)_nCHO \qquad \text{VII}$$

wherein $R^9$ represents a hydrogen atom or a suitable acid labile group and n is as hereinbefore defined. Suitable acid labile groups are those which are easily removed by acid hydrolysis and do not cause side reactions, e.g. the 2-tetrahydropyranyl radical unsubstituted or substituted by, for example, at least one lower alkyl group.

The process of the invention for the preparation of cyclopentane derivatives of general formula I wherein $R^1$, $R^2$ and n are as hereinbefore defined, the symbols $R^3$ represent hydrogen atoms, and $R^4$ represents a carboxy group, including 7-[2-hydroxy-5-(3-hydroxy-1-octenyl)cyclopentyl]heptanoic acid, is illustrated schematically as follows:

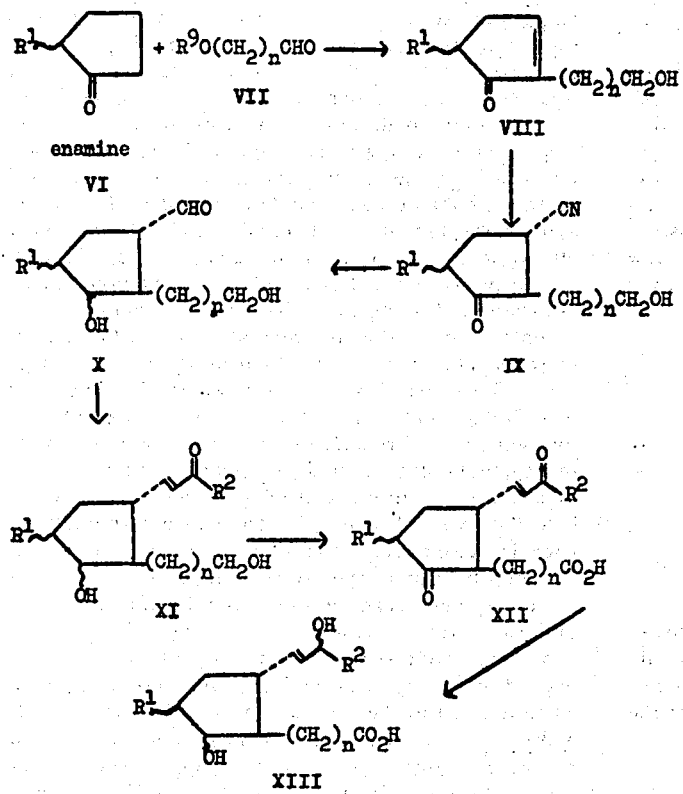

wherein $R^1$, $R^9$ and $n$ are as hereinbefore defined. This new process involves only six steps as depicted and is, in consequence, distinctly advantageous in relation to the known processes for the preparation of the same compounds.

The reaction of an enamine (e.g. the morpholine enamine) of the cyclopentanone of formula VI and an aldehyde of formula VII to yield the 2-hydroxyalkyl-2-cyclopenten-1-ones of formula VIII is carried out by heating in an inert organic solvent, for example an aromatic hydrocarbon (e.g. benzene) with continuous removal of water, preferably at 60°–120°C., followed by hydrolysis in aqueous acid conditions (e.g. with hydrochloric acid), preferably at ambient temperature, and then heating with an acid, (e.g. concentrated hydrochloric acid), preferably at about 100°C., and preferably in an inert organic solvent such as an alcohol (e.g. butanol) to cause the double bond to migrate from the exocyclic to the endocyclic position. The 2-hydroxyalkyl-2-cyclopenten-1-ones of formula VIII thus obtained are new products and are key intermediates of the new process of the invention.

The 2-hydroxyalkyl-2-cyclopenten-1-ones of formula VIII are reacted with a source of hydrogen cyanide (e.g. acetone cyanohydrin) in the presence of a base, for example an alkali metal carbonate (e.g. sodium carbonate), in an aqueous organic solvent, for example an aqueous lower alkanol (e.g. aqueous methanol), preferably at 50°–110°C. and advantageously at the reflux temperature of the solvent employed, to give ketonitriles of formula IX. These ketonitriles are reduced in an inert organic solvent, for example a lower dialkyl ether (e.g. diethyl ether), preferably at a temperature between −80° and +30°C., to 3-hydroxy-2-hydroxyalkyl-cyclopentanecarbaldehydes of formula X by means of known complex metal reducing agents, preferably a dialkylaluminium hydride (e.g. diisobutylaluminium hydride) in an inert organic solvent, for example an aromatic hydrocarbon (e.g. benzene). Reaction of compounds of formula X with an alkanoylmethylene triphenyl- or trialkylphosphorane of the general formula:

$$(Q)_3P=CH-CO-R^2 \qquad XIV$$

(wherein Q represents a phenyl group unsubstituted or substituted by a lower alkyl group, or represents a lower alkyl group, preferably n-butyl, and $R^2$ is as hereinbefore defined) in an inert organic solvent (e.g. tetrahydrofuran), preferably at a temperature of 20°–100°C. and advantageously at the reflux temperature of the reaction mixture, gives unsaturated ketones of formula XI. These ketones are then oxidised in an inert organic solvent, such as a ketone (e.g. acetone), by means of an agent known to convert hydroxy to oxo and a terminal hydroxymethyl to carboxy without affecting carbon-carbon double bonds (for example chromium trioxide in sulphuric acid in an inert organic solvent, e.g. acetone, preferably at a temperature of −5° to +25°C.) to give cyclopentanonealkanoic acids of formula XII. The cyclopentanonealkanoic acids, preferably in an inert organic solvent, for example a lower alkanol (e.g. ethanol), are reduced by means of an agent known for the reduction of oxo to hydroxy without affecting carbon-carbon double bonds, preferably by a metal borohydride (e.g. sodium borohydride) optionally in the presence of a base, for example an alkali metal hydroxide (e.g. aqueous sodium hydroxide), or by reaction with aluminium isopropoxide (e.g. at about 100°C.), when isopropanol is employed as the solvent medium, to yield as products the 2-hydroxy-5-(3-hydroxyalkenyl)-cyclopentyl-alkanoic acids of formula XIII.

The enamines of cyclopentanones of formula VI may be prepared from the cyclopentanone and a secondary amine, preferably in an aromatic hydrocarbon solvent (e.g. benzene or toluene), by the method of G. Stork et al., J. Am. Chem. Soc., 1963, 85, 207. Preferred secondary amines are 5- or 6-membered nitrogen-containing secondary heterocyclic bases, which may carry in the ring one or two additional hetero atoms selected from oxygen and nitrogen (e.g. morpholine). When the amine contains more than one nitrogen atom, one of the nitrogen atoms is secondary and the remainder are tertiary.

The aldehyde compounds of formula VII may be prepared by known methods, or by a process which comprises the reaction of a nitrile of the general formula:

$$R^9O(CH_2)_nCN \qquad XV$$

(wherein $n$ and $R^9$ are as hereinbefore defined) in an inert organic solvent such as a lower dialkyl ether (e.g. diethyl ether) with a dialkylaluminium hydride (e.g. diisobutylaluminium hydride) in an inert organic solvent, for example an aromatic hydrocarbon (e.g. benzene), preferably at a temperature of −80° to +30°C. The same aldehyde compounds may also be prepared by oxidation of a compound of the general formula:

$$R^{9'}O(CH_2)_nCH_2OH \qquad XVI$$

(wherein $n$ is as hereinbefore defined and $R^{9'}$ is an acid labile group, e.g. 2-tetrahydropyranyl) with an agent known to convert hydroxymethyl to formyl without affecting the ether linkage, for example dimethyl sulphoxide and pyridine sulphur trioxide complex at ambient temperature.

The cyclopentanones of formula VI and the nitriles of formula XV are readily available commercially or easily accessible by known methods. By the term "known methods" as used in this specification is meant methods heretofore used or described in the literature.

The alkanolymethylene phosphoranes of general formula XIV used in the above process for reaction with the 3-hydroxy-2-hydroxyalkylcyclopentanecarbaldehydes of formula X, which are new compounds and important intermediates, to give the unsaturated ketones of formula XI may be prepared by the reaction between a 1-chloro-2-alkanone of the formula:

$$ClCH_2—CO—R_2$$

(wherein $R^2$ is as hereinbefore defined) and an appropriate triphenyl- or trialkyl-phosphine in a suitable organic solvent (e.g. chloroform) under a nitrogen atmosphere, preferably at a temperature of 20°–100°C. and advantageously at the reflux temperature of the reaction mixture, followed by reaction of the resulting 2-oxoalkylphosphonium chloride with an inorganic base (e.g. aqueous sodium carbonate) at ambient temperature.

From the products of formula XIII of the aforedescribed process and intermediates obtained thereby of formulae XI and XII there can be prepared by application of known procedures other cyclopentane derivatives of general formula I which have not hitherto been described. These new cyclopentane derivatives are all those of general formula I wherein n represents 5, 7 or 8 and the various R symbols are as hereinbefore defined in relation to that formula, or n represents 6 and at least one of the various R symbols and X represents a group specified below:

$R^1$ is a lower alkyl group;

$R^2$ is a branched-chain alkyl group containing 3 to 10 carbon atoms;

$R^3$ is a lower alkyl, lower alkenyl or phenyl(lower)alkyl group;

$R^4$ is a group of the formula II, III or IV;

X is an epoxyethylene or cyclopropylene group, the other R symbols and X having any of the meanings hereinbefore defined in relation to general formula I. Such new cyclopentane derivatives, and their non-toxic salts when $R^4$ in general formula I represents a carboxy group, are a feature of the present invention. Within this class of new cyclopentane derivatives those wherein $R^1$ represents a hydrogen atom or a methyl group, $R^2$ represents a straight or branched-chain alkyl group containing 5, 6 or 7 carbon atoms, the symbols $R^3$ are the same and both represent hydrogen atoms, methyl or acetyl groups, $R^4$ represents a carboxy group or an N-methylcarbamoyl (i.e. —CONHCH$_3$), hydrazinocarbonyl (i.e. —CONHNH$_2$) or methoxycarbonyl (i.e. —COOCH$_3$) group, X represents a vinylene, ethylene, epoxyethylene or cyclopropylene group, and $n$ represents 5 or 6, and, when $R^4$ represents a carboxy group, non-toxic salts thereof, are preferred. Of outstanding importance are those such compounds wherein $R^2$ represents a secondary or tertiary alkyl group, i.e. an alkyl group branched at the carbon atom attached to the group —(CHOR$^3$)—.

The compounds of general formula I and their non-toxic salts possess valuable pharmacodynamic properties, in particular the production of hypotension, bronchodilation, inhibition of gastric acid secretion and stimulation of uterine contraction. Bronchodilator activity, i.e. the production of relaxation of the smooth muscle of the bronchial tree, is of value in the removal or reduction of the state of bronchospasm, thereby facilitating breathing, in patients suffering from conditions such as bronchial asthma, bronchitis, bronchiectasis and emphysema. In laboratory screening methods the compounds produce (i) a 10 mm.Hg fall in the mean blood pressure of the urethane-anaesthetized, pempidine-treated normotensive rat at doses between 0.04 and 4.0 mg./kg. animal body weight administered intravenously; (ii) a 50% inhibition of the bronchoconstriction induced by administration of a bronchoconstrictor agonist, e.g. histamine or 5-hydroxytryptamine, in the urethane-anaesthetized guinea-pig at doses between 0.005 and 3.0 mg./kg. animal body weight administered intravenously; (iii) a 50% inhibition of pentagastrin-induced gastric acid secretion in the rat at doses of between 1.0 and 50 µg/kg. animal body weight/minute when administered orally in solution in an aqueous sodium chloride solution; and (iv) at least a 50% increase in amplitude of contraction of the uterus of the pregnant rat when administered intravenously at doses between 0.5 and 10 mg./kg. body weight. The guinea-pig is generally considered to provide a reliable model for the human subject with good clinical correlation in the study of bronchodilators [Herxheimer, H. J. Physiol. London, 190, 41–42P (1967)].

It will be appreciated that the carboxy group of the 2-hydroxy-5-(3-hydroxyalkenyl)cyclopentyl-alkanoic acids of formula XIII can be converted by known methods into groups of formula II, III, IV or V, and that the two hydroxy groups in the compounds of formula XIII can be converted by known methods to groups —OR$^{3'}$, wherein $R^{3'}$ represents a lower alkyl, lower alkenyl, phenyl(lower)alkyl or lower alkanoyl group. From compounds so obtained other cyclopentanone derivatives of general formula I can be prepared.

Thus, compounds of general formula I wherein $R^3$ represents a lower alkyl, lower alkenyl or phenyl(lower)alkyl group, $R^4$ represents a group of formula II, III, IV or V, X represents a vinylene, ethylene or cyclopropylene group, can be prepared by the reaction of a compound of the formula $R^{3'''}$ Y (wherein $R^{3'''}$ represents a lower alkyl, lower alkenyl or phenyl(lower)alkyl group, and Y represents the acid residue of a reactive ester, e.g. a bromine, chlorine or iodine atom or a sulphonate or sulphate group) with a compound of the general formula:

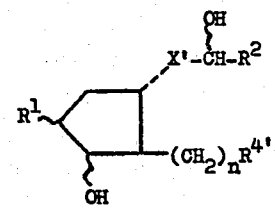
XVII (wherein $R^1$, $R^2$ and $n$ are as hereinbefore defined, $R^{4'}$ represents a group of formula II, III, IV or V, and X' represents a vinylene, ethylene or cyclopropylene group) optionally in an inert organic solvent, for example an aromatic hydrocarbon (e.g. benzene), in the presence of an alkali metal or alkaline earth metal hydride (e.g. sodium hydride) or a suitable metal oxide, preferably silver oxide, preferably at a temperature of 50°–150°C. Alternatively a compound of formula XVII can be reacted with a diazoalkane of the formula $R^{10}=N_2$ (wherein $R^{10}$ represents an alkylidene group containing from 1 to 4 carbon atoms) and a Lewis acid, e.g. boron trifluoride, in an inert organic solvent medium, preferably a dialkyl ether (e.g. diethyl ether), and preferably at a temperature between −50° and −20°C., to give compounds of general formula I wherein $R^3$ represents a lower alkyl group.

The products so obtained can, if desired, be hydrolysed, for example with an aqueous alkali (e.g. aqueous sodium hydroxide), preferably at a temperature of 40°–110°C., to give the corresponding free acids of general formula I wherein $R^4$ represents a carboxy group.

Compounds of general formula I wherein $R^1$, $R^2$, $R^3$ and $n$ are as hereinbefore defined, $R^4$ represents a group —COOR$^8$ ($R^8$ being as hereinbefore defined) and X represents a vinylene, ethylene or cyclopropylene group, can be prepared by the reaction of a corresponding compound of general formula I, in which $R^4$ represents a carboxy group, with an alcohol $R^8OH$ ($R^8$ being as hereinbefore defined), an excess of which may be employed as solvent medium, in the presence of an inorganic acid, e.g. hydrochloric acid or sulphuric acid, preferably at a temperature between 50° and 110°C. and advantageously at the reflux temperature of the reaction mixture, or with a diazoalkane $R^{10}=N_2$ ($R^{10}$ being as hereinbefore defined) in an inert organic solvent medium, preferably a dialkyl ether (e.g. diethyl ether), preferably at ambient temperature. Alternatively, a silver salt of such carboxylic acids of general formula I can be reacted with an alkyl halide $R^8$-Hal, wherein Hal represents a halogen atom and $R^8$ is as hereinbefore defined, optionally in the presence of an inert organic solvent such as an aromatic hydrocarbon (e.g. benzene) at elevated temperature and advantageously at the reflux temperature of the reaction mixture.

Compounds of general formula I wherein $R^3$ represents a lower alkanoyl group, $R^4$ represents a carboxy group or esterified carboxy group —COOR$^8$ ($R^8$ being as hereinbefore defined), and X represents a vinylene, ethylene or cyclopropylene group, can be prepared by the reaction of a corresponding compound of general formula I, in which $R^3$ represents a hydrogen atom, with a carboxylic acid anhydride of the formula $(R^{3'''})_2O$ (wherein $R^{3'''}$ represents a lower alkanoyl group) such as acetic anhydride, preferably in the presence of a base, e.g. pyridine, preferably at ambient temperature, optionally in the presence of an inert organic solvent such as an aromatic hydrocarbon (e.g. benzene).

Compounds of general formula I wherein $R^1$, $R^2$ and $n$ are as hereinbefore defined, $R^3$ represents a hydrogen atom or a lower alkyl, lower alkenyl or phenyl(lower)alkyl group, $R^4$ represents a group of formula II, III or IV, and X represents a vinylene, ethylene or cyclopropylene group, can be prepared by the reaction of a corresponding ester of general formula I, in which $R^4$ represents a group —COOR$^8$ ($R^8$ being as hereinbefore defined), with a compound of the general formula:

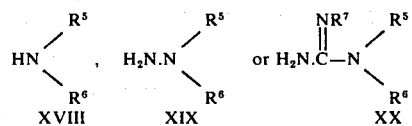

(wherein $R^5$, $R^6$ and $R^7$ are as hereinbefore defined) in an inert organic solvent, e.g. a lower alkanol (preferably ethanol), preferably at a temperature of 50°–100°C. and advantageously at the reflux temperature of the reaction mixture, optionally in the presence of a basic catalyst, for example an alkali metal alkoxide in a lower alkanol, e.g. sodium ethoxide in ethanol. Alternatively, the same such compounds of general formula I, except for those wherein $R^3$ represents a hydrogen atom, can be prepared by reacting a corresponding acid halide of general formula I (i.e. $R^4$ is a group —COHal, Hal being as hereinbefore defined) with a compound of formula XVIII, XIX or XX, optionally in an inert organic solvent, for example a di(lower)alkyl ether, preferably at ambient temperature.

Compounds of general formula I wherein $R^1$, $R^2$, $R^3$, $R^4$ and $n$ are as hereinbefore defined and X represents an ethylene group, can be prepared by hydrogenation of a corresponding compound of general formula I, in which X is a vinyl group, or in respect of those compounds wherein $R^3$ represents a hydrogen atom a compound of the general formula:

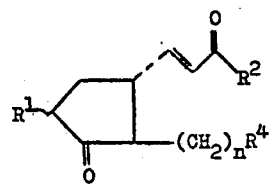
XXI (wherein $R^1$, $R^2$ and $R^4$ are as hereinbefore defined), using a suitable catalyst such as Rancy nickel or palladium on charcoal, or by an initial reduction of the carbon-carbon double bond in a compound of formula XXI with hydrogen and a catalyst followed, if necessary, by further reduction to reduce the carbonyl groups to hydroxy groups, for example with a metal borohydride (e.g. sodium borohydride), preferably in an inert organic solvent, for example a lower alkanol (e.g. ethanol), preferably at a temperature of 0° to 25°C. and optionally in the presence of a base, for example an alkali metal hydroxide (e.g. aqueous sodium hydroxide).

Alternatively, compounds of general formula I, wherein $R^1$, $R^2$ and $n$ are as hereinbefore defined, $R^3$ represents a hydrogen atom, $R^4$ represents a carboxy group and X represents an ethylene group, can be prepared from the unsaturated ketones of formula XI by catalytic reduction of the carbon-carbon double bond using a suitable catalyst such as Raney nickel or palladium on charcoal, followed by oxidation of the terminal hydroxymethyl group in the resulting product to carboxy (and, where the keto group is reduced in the preceding operation to a hydroxy group, the oxidation of the hydroxy group back to keto) by means of an agent known for such an oxidation (for example chromium trioxide in sulphuric acid in an inert organic solvent, e.g. acetone), and then reduction of the two keto groups in the resulting cyclopentanonealkanoic acid to hydroxy groups by means known for the conversion of a keto group to hydroxy in the presence of a carboxy group, for example hydrogenation in the presence of a catalyst or by a metal borohydride in the presence of a base, as hereinbefore mentioned.

Compounds of general formula I wherein $R^1$, $R^2$, $R^3$, $R^4$ and $n$ are as hereinbefore defined and X represents an epoxyethylene group, can be prepared from a corresponding compound of general formula I, in which X represents a vinylene group, by the action of an organic peracid (e.g. perbenzoic acid) in an inert organic solvent (e.g. chloroform), preferably at a temperature of 20°-100°C.

Compounds of general formula I wherein $R^1$, $R^2$, $R^3$, $R^4$ and $n$ are as hereinbefore defined and X represents a cyclopropylene group, can be prepared from a corresponding compound of general formula I, in which X represents a vinylene group, by the action of a methylene dihalide (preferably dibromide or diiodide) and a zinc/copper couple, in an inert organic solvent (e.g. diethyl ether), preferably at a temperature of 20°-100°C, and advantageously at the reflux temperature of the reaction mixture. Alternatively, the same such compounds of general formula I, wherein $R^3$ represents a hydrogen atom and $R^4$ represents a carboxy group, can be prepared by reacting an unsaturated ketone of formula XI with a suitable methylene transfer agent (e.g. dimethyl sulphoxonium methylide, preferably in an inert organic solvent such as diethyl ether, for example at a temperature of 20°-70°C.), followed by oxidation of the resulting intermediate to the corresponding diketo acid and reduction to the di-alcohol as hereinbefore described in the conversion of compounds of formula XI to those of formula XIII.

By "non-toxic salts" of the cyclopentanone derivatives of general formula I is meant salts the cations of which are relatively innocuous to the animal organisms when used in therapeutic doses so that the beneficial pharmacological properties of the parent compound of general formula I are not vitiated by side-effects ascribable to those cations. Preferably, the salts are water-soluble. Suitable salts include the alkali metal, e.g. sodium or potassium, and ammonium salts and pharmaceutically-acceptable (i.e. non-toxic) amine salts.

Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from alkyl groups containing from 1 to 6 carbon atoms, hydroxyalkyl groups containing from 1 to 3 carbon atoms, cycloalkyl groups containing from 3 to 6 carbon atoms, phenyl groups, phenylalkyl groups containing from 7 to 11 carbon atoms and phenylalkyl groups containing from 7 to 15 carbon atoms wherein the alkyl moieties are substituted by hydroxy groups. The alkyl moieties of such alkyl and phenylalkyl groups may be straight or branched chains and the phenyl group and phenyl moieties of phenylalkyl groups may be unsubstituted or substituted by one or two straight- or branched-chain alkyl groups containing from 1 to 6 carbon atoms. Suitable amines also include those derived in theory by the replacement of two of the hydrogen atoms of ammonia by a hydrocarbon chain, which may be interrupted by nitrogen, oxygen or sulphur atoms, to form, together with the nitrogen atom of ammonia to which its terminal groups are attached, a five- or six-membered nitrogen-containing heterocyclic ring, which heterocyclic ring may be unsubstituted or substituted by one or two straight- or branched-chain alkyl groups containing from 1 to 6 carbon atoms. Examples of suitable amine cations include mono-, di- and tri-methylammonium, mono-, di- and tri-ethylammonium, mono-, di- and tri-propylammonium, mono-, di- and tri-isopropylammonium, ethyldimethylammonium, mono-, di- and tri-2-hydroxyethylammonium, ethyl bis-(2-hydroxyethyl)ammonium, butylmono(2-hydroxyethyl)ammonium, tris(hydroxymethyl)ammonium, cyclohexylammonium, benzylammonium, benzyldimethylammonium, dibenzylammonium, phenyl-2-hydroxyethylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-butylpiperidinium, 2-methylpiperidinium and 1-ethyl-2-methylpiperidinium.

The non-toxic salts may be prepared by reaction of stoichiometric quantities of compounds of general formula I wherein $R^4$ represents a carboxy group and the appropriate base, e.g. an alkali metal hydroxide or carbonate, ammonium hydroxide, ammonia or an amine in a suitable solvent which is preferably water in the case of the preparation of alkali metal salts and water or isopropanol in the case of ammonium or amine salts. The salts may be isolated by lyophilisation of the solution or, if sufficiently insoluble in the reaction medium, by filtration, if necessary after removal of part of the solvent.

The following Examples illustrate the process of the present invention and the preparation of new cyclopentane derivatives of general formula I.

EXAMPLE 1

7-[2-Hydroxy-5-(3-hydroxy-1-octenyl)cyclopentyl]-heptanoic acid i. Preparation of 2-(7-hydroxyheptyl)-2-cyclopenten-1-one A mixture of 7-(2-tetrahydropyranyloxy)heptanal (22 g., 0.1 mole) and 1-morpholinocyclopentene, i.e. the morpholine enamine of cyclopentanone, (21.4 g., 0.14 mole) in benzene (25 ml.) was heated under reflux for 12 hours under nitrogen, and the water liberated was continuously removed with a Dean and Stark head. Benzene (10 ml.) and then, dropwise, 18% hydrochloric acid (28 ml.) were added and the mixture was stirred for 2 hours. The organic layer was separated and evaporated. Concentrated hydrochloric acid (72 ml.) and butanol (300 ml.) were added to the residue. The mixture was heated at 100°C. for 1 hour, and then the solution was concentrated to give an oil. Diethyl ether was added, and the ether solution was washed with aqueous sodium bicarbonate and then water, and dried over sodium sulphate. The solvent was evaporated and the residue was distilled under reduced pressure to give 2-(7-hydroxyheptyl)-2-cyclopenten-1-one (11.7 g., 60%), b.p. 125°–170° C./0.15 mm.Hg, $n_D^{25}$ 1.490, $\lambda_{max}$228 m$\mu$ (ethanol).

ii. Preparation of 2-(7-hydroxyheptyl)-3-oxocyclopentanecarbonitrile

A mixture of 2-(7-hydroxyheptyl)-2-cyclopenten-1-one (17 g., 0.087 mole), acetone cyanohydrin (8.5 g., 0.1 mole), 6% aqueous sodium carbonate (8 ml.) and methanol (50 ml.) was stirred and heated under reflux for 4 hours. Methanol was removed in vacuo, water (100 ml.) was added and the mixture was extracted with diethyl ether and dried over magnesium sulphate. The solvent was removed by evaporation, and the residue was distilled under reduced pressure to give 2-(7-hydroxyheptyl)-3-oxocyclopentanecarbonitrile (13.3 g., 68%), b.p. 144°–182°C./0.15 mm.Hg, $n_D^{25}$ 1.4795.

iii. Preparation of 3-hydroxy-2-(7-hydroxyheptyl)cyclopentanecarbaldehyde

A solution of diisobutylaluminium hydride (25.6 g., 0.18 mole) in benzene (250 ml.) was added, with rapid stirring, to a solution of 2-(7-hydroxyheptyl)-3-oxocyclopentanecarbonitrile (10 g., 0.045 mole) in dry diethyl ether (250 ml.) at 10°–15°C. Stirring at ambient temperature was contined for 15 minutes and the mixture was added to 2N aqueous acetic acid (300 ml.) at a temperature lower than 15°C. The organic phase was separated and the aqueous layer was extracted with diethyl ether. The combined organic phases were washed with aqueous sodium bicarbonate, dried over magnesium sulphate and the solvents were removed in vacuo. The residue was distilled under reduced pressure to give 3-hydroxy-2-(7-hydroxyheptyl)cyclopentanecarbaldehyde (4.5 g., 43%), b.p. 185°–193°C./0.1 mm.Hg, $n_D^{22.5}$ 1.4995.

iv. Preparation of 2-(7-hydroxyheptyl)-3-(3-oxo-1-octenyl)cyclopentanol

A mixture of 3-hydroxy-2-(7-hydroxyheptyl)cyclopentanecarbaldehyde (4.5 g., 0.02 mole) and hexanoylmethylene triphenylphosphorane (7.5 g., 0.02 mole) in dry tetrahydrofuran (100 ml.) was heated under reflux for 6 hours. The solvent was removed in vacuo and the residue was chromatographed on silica gel. Elution with a 3:2 mixture of petrol (b.p. 40°–60°C.) and ethyl acetate gave 2-(7-hydroxyheptyl)-3-(3-oxo-1-octenyl)cyclopentanol (4 g., 63%), $\lambda_{max}$230 m$\mu$, $\epsilon$ 12,900 (ethanol), $\nu_{max}$1660 cm$^{-1}$, 1620 cm$^{-1}$ (liquid film).

Hexanoylmethylene triphenylphosphorane, used as starting material, was prepared as follows:

A solution of 1-chloro-2-heptanone (33 g.) and triphenylphosphine (60 g.) in chloroform (50 ml.) was saturated with nitrogen and refluxed under nitrogen overnight. The chloroform was removed in vacuo and the residue was dissolved in methylene chloride (150 ml.). Dry diethyl ether (600 ml.) was added to precipitate 2-oxoheptyltriphenylphosphonium chloride (60 g.), m.p. 165°–168°C. This compound (23 g.) was added portionwise to a solution of sodium carbonate (25 g.) in water (250 ml.), and the mixture was stirred vigorously for 24 hours. The solution was extracted with diethyl ether, and the ethereal extracts were dried over magnesium sulphate. The solvent was removed by evaporation and the residue was cooled and triturated with petrol (b.p. 40°–60°C.). The solid thus obtained was recrystallised from petrol (b.p. 60°–80°C.) to give hexanoylmethylene triphenylphosphorane (17 g.), m.p. 73°–74°C.

v. Preparation of 7-[2-oxo-5-(3-oxo-1-octenyl)cyclopentyl]heptanoic acid.

8N Jones' reagent (3.24 ml.; J. Chem. Soc., 1953, 461) was added to a stirred solution of 2-(7-hydroxyheptyl)-3-(3-oxo-1-octenyl)cyclopentanol (1.4 g., 0.0043 mole) in acetone (10 ml.) at 15°–25°C., at a rate such that the deep red coloration caused by the addition of one drop of reagent had changed to green before addition of the next drop. The reaction mixture was diluted with sufficient water to dissolve the precipitated chromium salts, and was then extracted three times with diethyl ether. The combined ether extracts were washed with 2N aqueous sulphuric acid and then added to 10% aqueous sodium carbonate (100 ml.) and stirred for 1 hour. The aqueous layer (containing the desired acid as the sodium salt) was separated and washed with diethyl ether. The solution was then covered with a layer of diethyl ether, cooled to below 20°C. and acidified to pH 1 by the dropwise addition of concentrated hydrochloric acid. The ether layer was separated and the aqueous layer was again extracted with diethyl ether. The combined extracts were dried over magnesium sulphate, and the other was removed in vacuo to give the crude acid (0.79 g.). This was purified by preparative thin layer chromatography on silica gel using a 65:15:1 mixture of benzene, dioxane and acetic acid as solvent. Evaporation gave pure 7-[2-oxo-5-(3-oxo-1-octeny)cyclopentyl]heptanoic acid (0.38 g., 26%), $\lambda_{max}$228 m$\mu$, $\epsilon$ 11,600 (ethanol), $\nu_{max}$1730 cm$^{-1}$, 1700 cm$^{-1}$, 1670 cm$^{-1}$, 1625 cm$^{-1}$ and 980 cm$^{-1}$ (liquid film). N.M.R. (approximately 10% solution in deuterochloroform) 0.9 $\delta$(triplet J=5c/s, terminal CH$_3$), 1.2–2.0 $\delta$(overlapping multiplets, cyclic and chain CH$_2$), 2.0–2.8 $\delta$ (multiplet CH$_2$C=O), 6.17 $\delta$ (doublet J=16c/s, CH=CHC=O) and 6.8 $\delta$ (doublet of doublets J=16c/s and

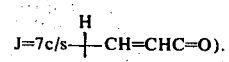

vi. Preparation of 7-[2-hydroxy-5-(3-hydroxy-1-octenyl)cyclopentyl]-heptanoic acid A solution of sodium borohydride (0.035 g., 0.0009 mole) in 0.2N aqueous sodium hydroxide (0.35 ml.) was added dropwise to a solution of 7-[2-oxo-5-(3-oxo- 1-octenyl)cyclopentyl]heptanoic acid (0.14 g., 0.0004 mole) in ethanol (3 ml.) and N aqueous sodium hydroxide (0.42 ml., 0.0004 mole). The resulting solution was stirred for 1 day, and then the ethanol was removed in vacuo. A small quantity of water was added, and the solution was extracted twice with diethyl ether (to remove non-acidic material). The aqueous solution was covered with a layer of diethyl ether and acidified to pH 1 by the dropwise addition of concentrated hydrochloric acid, cooling the solution to about 10°C. The ether layer was separated and the aqueous layer extracted twice more with diethyl ether. The combined ether extracts were dried over magnesium sulphate and evaporated to give 7-[2-hydroxy-5-(3-hydroxy-1-octenyl)cyclopentyl]heptanoic acid (0.08 g., 57%), $\nu_{max}$ 1700 cm$^{-1}$ and 980 cm$^{-1}$ (liquid film), which required no further purification. N.M.R. (approximately 10% solution in deuterochloroform) 0.9 δ (triplet J=5c/s, terminal CH$_3$), 1.1–2.0 δ (broad band, cyclic and chain CH$_2$), 2.3 δ (triplet J=6c/s, CH$_2$C=O) ~ 4.0 δ (broad mutiplet

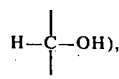

5.25 δ (broad singlet, OH), 5.4δ (broad peak

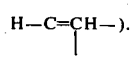

The 7-(2-tetrahydropyranyloxy)heptanal used as starting material in the above Example was prepared as follows:

3,4-Dihydro-2H-pyran (272 g., 3.35 mole) was added dropwise at 40°C. with stirring to 7-hydroxyheptanenitrile (284 g., 2.24 mole) and concentrated hydrochloric acid (10 drops). The temperature was allowed to rise to 65°C. and was maintained at this level for one hour. The solution was cooled and benzene (500 ml.) was added. The solution was washed with aqueous sodium bicarbonate and then water, and dried over sodium sulphate. The solvent was removed in vacuo, and the residue distilled under reduced pressure to give 7-(2-tetrahydropyranyloxy)heptanenitrile (411 g., 87%), b.p. 100°–130°C./0.1 mm.Hg, n$_D^{25}$ 1.455.

Diisobutylaluminium hydride (19.4 g., 0.14 mole) in dry benzene (50 ml.) was added dropwise at 10°C. to a stirred solution of 7-(2-tetrahydropyranyloxy)heptanenitrile (20.6 g., 0.1 mole) in dry diethyl ether (200 ml.). The solution was stirred at 10°C. for 30 minutes and was then added to 2N aqueous sulphuric acid (300 ml.) at 0°C. The mixture was heated at 30°C. for 30 minutes, and then saturated with sodium chloride and the layers were separated. The aqueous layer was extracted with diethyl ether and the combined organic layers were washed with aqueous sodium bicarbonate, and then aqueous sodium chloride, and dried over sodium sulphate. The solvent was evaporated and the residue was distilled under reduced pressure to give 7-(2-tetrahydropyranyloxy)heptanal (12.7 g., 66%), b.p. 78°–106°C./0.1 mm.Hg, n$_D^{25}$ 1.456.

The above procedure may also be carried out replacing the 7-(2-tetrahydropyranyloxy)heptanal by 7-hydroxyheptanal [prepared as described above for 7-(2-tetrahydropyranyloxy)heptanal, but using 7-hydroxyheptanenitrile in place of 7-(2-tetrahydropyranyloxy)heptanenitrile].

EXAMPLE 2

7-[2-Hydroxy-5-(3-hydroxy-1-octenyl)-3-methylcyclopentyl]heptanoic acid i. Preparation of 2-(7-hydroxyheptyl)-5-methyl-2-cylcopenten-1-one

A mixture of 7-(2-tetrahydropyranyloxy)heptanal (22 g., 0.1 mole) and the morpholine enamine of 2-methylcyclopentanone (20.2 g., 0.12 mole) in benzene (25 ml.) was heated under reflux for 12 hours under nitrogen, and the water liberated was continuously removed with a Dean and Stark head. Benzene (10 ml.) and then, dropwise, 18% hydrochloric acid (24 ml.) were added and the mixture was stirred for 2 hours. The organic layer was separated and evaporated. Concentrated hydrochloric acid (72 ml.) and butanol (300 ml.) was added to the residue. The mixture was heated at 100°C. for 1 hour and then the solution was concentrated to give an oil. Diethyl ether was added, and the ether solution was washed with aqueous sodium bicarbonate and then water, and dried over sodium sulphate. The solvent was evaporated and the residue was distilled under reduced pressure to give an approximately equimolar mixture of 2-(7-hydroxyheptyl)-5-methyl-2-cyclopenten-1-one and 5-(7-hydroxyheptyl)-2-methyl-2-cyclopenten-1-one (12 g., 57%), b.p. 130°–170°C./0.12 mm. Hg, λ$_{max}$ 228mµ (ethanol).

ii. Preparation of 2-(7-hydroxyheptyl)-4-methyl-3-oxocyclopentanecarbonitrile An approximately equimolar mixture of 2-(7-hydroxyheptyl)-5-methyl-2-cyclopenten-1-one and 5-(7-hydroxyheptyl)-2-methyl-2-cyclopenten-1-one, (31.5 g., 0.15 mole), acetone cyanohydrin (14.4 g., 0.17 mole), 6% aqueous sodium carbonate (13.6 ml.) and methanol (90 ml.) was stirred and heated under reflux for 4 hours. Methanol was removed in vacuo, water (150 ml.) added and the mixture was extracted with diethyl ether and dried over magnesium sulphate. The solvent was removed by evaporation and the residue was distilled under reduced pressure to give a mixture of 2-(7-hydroxyheptyl)-4-methyl-3-oxocyclopentanecarbonitrile and 4-(7-hydroxyheptyl)-2-methyl-3-oxocyclopentanecarbonitrile (25.8 g., 49%), b.p. 150°–200°C./0.15 mm.Hg.

iii. Preparation of 3-hydroxy-2-(7-hydroxyheptyl)-4-methylcyclopentanecarbaldehyde A solution of diisobutylaluminium hydride (58 g., 0.41 mole) in benzene (500 ml.) was added, with rapid stirring, to a solution of a mixture of 2-(7-hydroxyheptyl)-4-methyl-3-oxocyclopentanecarbonitrile and 4-(7-hydroxyheptyl)-2-methyl-3-oxocyclopentanecarbonitrile (25.8 g., 0.109 mole) in dry diethyl ether (500 ml.) at 10°–15°C. Stirring at ambient temperature was continued for 15 minutes and the mixture was added to 2N aqueous acetic acid (500 ml.) at a temperature lower than 15°C. The organic phase was separated and the aqueous layer was extracted with diethyl ether. The combined organic phases were washed with aqueous sodium bicarbonate, dried over magnesium sulphate and the solvents were removed in vacuo. The residue was distilled under reduced pressure to give a mixture of 3-hydroxy-2-(7-hydroxyheptyl)-4-methylcyclopentanecarbaldehyde and 3-hydroxy-4-(7-hydroxyheptyl)-2-methylcyclopentanecarbaldehyde (8.4 g., 32%), b.p. 185°–198°C./0.15 mm.Hg.

iv. Preparation of 2-(7-hydroxyheptyl)-5-methyl-3-(3-oxo-1-octenyl)cyclopentanol A mixture of 3-hydroxy-2-(7-hydroxyheptyl)-4-methylcyclopentanecarbaldehyde and 3-hydroxy-4-(7-hydroxyheptyl)-2-methylcyclopentanecarbaldehyde (8.4 g., 0.035 mole) and hexanoylmethylene -triphenylphosphorane (16 g., 0.043 mole) in dry tetrahydrofuran (80 ml.) was heated under reflux for 6 hours. The solvent was removed in vacuo and the residue was chromatographed on silica gel. Elution with a 3:2 mixture of petrol (b.p. 40°–60°C.) and ethyl acetate gave a mixture of 2-(7-hydroxyheptyl)-5-methyl-3-(3-oxo-1-octenyl)cyclopentanol and 5-(7-hydroxyheptyl)-2-methyl-3-(3-oxo-1-octenyl)cyclopentanol (5.3 g., 45%), $\nu_{max}$ 1660 cm$^{-1}$, 1620 cm$^{-1}$ (liquid film).

v. Preparation of 7-[3-methyl-2-oxo-5-(3-oxo-1-octenyl)-cyclopentyl]-heptanoic acid 8N Jones' reagent (11.6ml.) was added to a stirred solution of a mixture of 2-(7-hydroxyhoptyl)-5-methyl-3-(3-oxo-1-octenyl)cyclopentanol and 5-(7-hydroxyheptyl)-2-methyl-3-(3-oxo-1-octenyl)cyclopentanol (5.2 g., 0.0154 mole) in acetone (35 ml.) at 15°–25°C., at a rate such that the deep red coloration caused by the addition of one drop of reagent had changed to green before addition of the next drop. The reaction mixture was diluted with sufficient water to dissolve the precipitated chromium salts, and was then extracted three times with diethyl ether. The combined ether extracts were washed with 2N aqueous sulphuric acid and then added to 10% aqueous sodium carbonate (200 ml.) and stirred for 1 hour. The aqueous layer (containing the desired acid as the sodium salt) was separated and washed with diethyl ether. The solution was then covered with a layer of diethyl ether cooled to below 20°C. and acidified to pH 1 by the dropwise addition of concentrated hydrochloric acid. The ether layer was separated and the aqueous layer was again extracted with diethyl ether. The combined extracts were dried over magnesium sulphate, and the ether was removed in vacuo to give the crude acid (3.45 g.). This was purified by preparative thin layer chromatography on silica gel using a 65:15:1 mixture of benzene, dioxane and acetic acid as solvent. Evaporation gave pure 7-[3-methyl-2-oxo-5-(3-oxo-1-octenyl)cyclopentyl]-heptanoic acid (1.03 g., 19%) $\lambda_{max}$ 228 m$\mu$, $\epsilon$ 12,100 (ethanol), $\nu_{max}$ 1730 cm$^{-1}$, 1700 cm$^{-1}$, 1670 cm$^{-1}$ and 1625 cm$^{-1}$ (liquid film). N.M.R. (approximately 10% solution in deuterochloroform) 0.89 $\delta$ (triplet J=5½c/s, terminal CH$_3$), 1.06 and 1.11 $\delta$ (two doublets J=6c/s, ring methyl), 1.35 $\delta$ (multiplet, chain CH$_2$), ~2.1 $\delta$ (multiplet, CH—C=C), 2–2.7 $\delta$ (multiplet, CH$_2$CO), 6.17 and 6.75 $\delta$ (doublet J=16c/s and doublet of doublets J=16c/s and 8c/s, CH=CHCO), 10.22 $\delta$ (singlet COOH). (Found: C, 72.3; H, 9.8. C$_{21}$H$_{34}$O$_4$ requires C, 72.0; H, 9.8%).

vi. Preparation of 7-[2-hydroxy-5-(3-hydroxy-1-octenyl)-3-methylcyclopentyl]heptanoic acid A solution of sodium borohydride (0.18 g., 0.0046 mole) in 0.2N aqueous sodium hydroxide (1.8 ml.) was added dropwise to a solution of 7-[3-methyl-2-oxo-5-(3-oxo-1-octenyl)cyclopentyl]heptanoic acid (0.5 g., 0.0014 mole) in ethanol (15 ml.) and N aqueous sodium hydroxide (1.4 ml., 0.0014 mole). The resulting solution was stirred for 1 day, and then the ethanol was removed in vacuo. A small quantity of water was added, and the solution was extracted twice with diethyl ether (to remove non-acidic material). The aqueous solution was covered with a layer of diethyl ether and acidified to pH 1 by the dropwise addition of concentrated hydrochloric acid, cooling the solution to about 10°C. The ether layer was separated and the aqueous layer extracted twice more with diethyl ether. The combined ether extracts were dried over magnesium sulphate and evaporated to give 7-[2-hydroxy-5-(3-hydroxy-1-octenyl)-3-methylcyclopentyl]heptanoic acid (0.4 g., 80%) which required no further purification. N.M.R. (approximately 10% solution in deuterochloroform), 0.84 $\delta$ (triplet J=5c/s, terminal CH$_3$), 0.95 $\delta$ (doublet J=6c/s, ring methyl), 1.31 $\delta$ (multiplet, chain CH$_2$), 2.24 $\delta$ (triplet J=6c/s, CH$_2$CO), 3.68 and 3.98 $\delta$ (overlapping multiplets, HCOH), 5.39 $\delta$ (multiplet CH=CH), 5.77 $\delta$ (singlet OH and COOH). (Found: C, 71.1; H, 10.7. C$_{21}$H$_{38}$O$_4$ requires C, 71.2; H, 10.8%).

EXAMPLE 3

6-[2-Hydroxy-5-(3-hydroxy-1-octenyl)cyclopentyl]-hexanoic acid i. Preparation of 2-(6-hydroxyhexyl)-2-cyclopenten-1-one A mixture of 6-(2-tetrahydropyranyloxy)hexanal (23.2 g., 0.116 mole) and 1-morphdinocyclopentene (25.5 g., 0.16 mole) in benzene (30 ml.) was heated under reflux for 12 hours under nitrogen, and the water liberated was continuously removed with a Dean and Stark head. Benzene (12 ml.) and then, dropwise, 18% hydrochloric acid (28 ml.) were added and the mixture was stirred for 2 hours. The organic layer was separated and evaporated. Concentrated hydrochloric acid (84 ml.) and butanol (350 ml.) were added to the residue. The mixture was heated at 100°C. for 1 hour, and then the solution was concentrated to give an oil. Diethyl ether was added, and the ether solution was washed with aqueous sodium bicarbonate and then water, and dried over sodium sulphate. The solvent was evaporated and the residue was distilled under reduced pressure to give 2-(6-hydroxyhexyl)-2-cyclopenten-1-one (10.7 g., 50%), b.p. 105°–160°C./15 mm.Hg, n$_D^{25}$ 1.491.

ii. Preparation of 2-(6-hydroxyhexyl)-3-oxocyclopentane-carbonitrile

A mixture of 2-(6-hydroxyhexyl)-2-cyclopenten-1-one (10.5 g., 0.058 mole), acetone cyanohydrin (5.6 g., 0.065 mole), 6% aqueous sodium carbonate (5.2 ml.) and methanol (35 ml.) was stirred and heated under reflux for 4 hours. Methanol was removed in vacuo, water (70 ml.) was added and the mixture was extracted with diethyl ether and dried over magnesium sulphate. The solvent was removed by evaporation and the residue was distilled under reduced pressure to give 2-(6-hydroxyhexyl)-3-oxocyclopentanecarbonitrile (8.8 g., 73%), b.p. 135°–178°C./0.15 mm.Hg, $n_D^{25}$ 1.4812.

iii. Preparation of 3-hydroxy-2-(6-hydroxyhexyl)cyclopentanecarbaldehyde

A solution of diisobutylaluminum hydride (19.3 g., 0.125 mole) in benzene (170 ml.) was added, with rapid stirring, to a solution of 2-(6-hydroxyhexyl)-3-oxocyclopentanecarbonitrile (8.8 g., 0.042 mole) in dry diethyl ether (200 ml.) at 10°–15°C. Stirring at ambient temperature was continued for 15 minutes and the mixture was added to 2N aqueous acetic acid (170 ml.) at a temperature lower than 15°C. The organic phase was separated and the aqueous layer was extracted with diethyl ether. The combined organic phases were washed with aqueous sodium bicarbonate, dried over magnesium sulphate and the solvents were removed in vacuo to give crude 3-hydroxy-2-(6-hydroxyhexyl)cyclopentanecarbaldehyde (8.6 g.). It was used without further purification.

iv. Preparation of 2-(6-hydroxyhexyl)-3-(3-oxo-1-octenyl)cyclopentanol

A mixture of 3-hydroxy-2-(6-hydroxyhexyl)cyclopentanecarbaldehyde (8.6 g.) and hexanoylmethylene triphenylphosphorane (16 g., 0.043 mole) in dry tetrahydrofuran (100 ml.) was heated under reflux for 6 hours. The solvent was removed in vacuo and the residue was chromatographed on silica gel. Elution with a 3:2 mixture of petrol (b.p. 40°–60°C.) and ethyl acetate gave 2-(6-hydroxyhexyl)-3-(3-oxo-1-octenyl)-cyclopentanol (8 g.), $\nu_{max}$ 1660 cm$^{-1}$, 1620 cm$^{-1}$ (liquid film).

v. Preparation of 6-[2-oxo-5-(3-oxo-1-octenyl)-cyclopentyl]hexanoic acid

8N Jones' reagent (19.4 ml.) was added to a stirred solution of 2-(6-hydroxyhexyl)-3-(3-oxo-1-octenyl)cyclopentanol (8.0 g., 0.026 mole) in acetone (60 ml.) at 15°–25°C. at a rate such that the deep red coloration caused by the addition of one drop of reagent had changed to green before addition of the next drop. The reaction mixture was diluted with sufficient water to dissolve the precipitated chromium salts and was then extracted three times with diethyl ether. The combined ether extracts were washed with 2N aqueous sulphuric acid and then added to 10% aqueous sodium carbonate (350 ml.) and stirred for 1 hour. The aqueous layer (containing the desired acid as the sodium salt) was separated and worked with diethyl ether. The solution was then covered with a layer of diethyl ether, cooled to below 20°C. and acidified to pH 1 by the dropwise addition of concentrated hydrochloric acid. The ether layer was separated and the aqueous layer was again extracted with diethyl ether. The combined extracts were dried over magnesium sulphate, and the ether was removed in vacuo to give the crude acid (4.62 g.). This was purified by preparative thin layer chromatography on silica gel using a 65:15:1 mixture of benzene, dioxane and acetic acid as solvent. Evaporation gave pure 6-[2-oxo-5-(3-oxo-1-octenyl)cyclopentyl]hexanoic acid (1.66 g., 20%) $\lambda_{max}$ 228 m$\mu$, $\epsilon$ 13,200 (ethanol), $\nu_{max}$ 1730 cm$^{-1}$, 1700 cm$^{-1}$, 1670 cm$^{-1}$ and 1625 cm$^{-1}$ (liquid film). N.M.R. (approximately 10% solution in deuterochloroform) 0.89 $\delta$ (triplet J=5½c/s, terminal CH$_3$), 1.4 $\delta$ (multiplet, chain CH$_2$), 2–2.7 $\delta$ (multiplets), 6.15 and 6.75 $\delta$ (doublet J=16c/s and doublet of doublets J=16c/s and 7½c/s, CH=CHCO), 10.15 $\delta$ (singlet, COOH). (Found: C, 70.4; H, 9.3. C$_{19}$H$_{30}$O$_4$ requires C, 70.8; H, 9.3%).

vi. Preparation of 6-[2-hydroxy-5-(3-hydroxy-1-octenyl)-cyclopentyl]-hexanoic acid A solution of sodium borohydride (0.2 g., 0.005 mole) in 0.2N aqueous sodium hydroxide (2 ml.) was added dropwise to a solution of 6-[2-oxo-5-(3-oxo-1-octenyl)cyclopentyl]hexanoic acid (0.61 g., 0.0019 mole) in ethanol (15 ml.) and N aqueous sodium hydroxide (1.9 ml., 0.0019 mole). The resulting solution was stirred for 1 day and then the ethanol was removed in vacuo. A small quantity of water was added and the solution was extracted twice with diethyl ether (to remove non-acidic material). The aqueous solution was covered with a layer of diethyl ether and acidified to pH 1 by the dropwise addition of concentrated hydrochloric acid, cooling the solution to about 10°C. The ether layer was separated and the aqueous layer extracted twice more with diethyl ether. The combined ether extracts were dried over magnesium sulphate and evaporated to give 6-[2-hydroxy-5-(3-hydroxy-1-octenyl)cyclopentyl]-hexanoic acid (0.53 g., 86%) which required no further purification. N.M.R. (approximately 10% solution in deuterochloroform) 0.82 $\delta$ (triplet J=5½c/s, terminal CH$_3$), 1.32 $\delta$ (multiplet, chain CH$_2$), 1.63 $\delta$ (multiplet CH–C–C), 2.30 $\delta$ (triplet J=6½c/s, CH$_2$CO), 3.6–4.3 $\delta$ (overlapping multiplets, HCOH), 4.90 $\delta$ (singlet OH and COOH), 5.41 $\delta$ (multiplet, CH=CH). (Found: C, 69.7; H, 10.5. C$_{19}$H$_{34}$O$_4$ requires C, 69.9; H, 10.5%).

The 6-(2-tetrahydropyranyloxy)hexanal used as starting material in this Example was prepared as follows:

6-(2-Tetrahydropyranyloxy)hexanol was prepared by a modification of the method described by Bohlmann, Jeute and Reinecke, Chem. Ber., 1969, 102, 3283. 3,4-Dihydro-2-H-pyran (33.6 g., 0.4 mole) was added dropwise at 30°C. with stirring to hexane-1,6-diol (47.2 g., 0.4 mole) in chloroform (500 ml.) and concentrated hydrochloric acid (30 drops). The temperature was allowed to rise to 40°C. and maintained at this level for 3 hours. The solution was then washed with aqueous sodium bicarbonate and then water and dried over potassium carbonate. The solvent was removed in vacuo, and the residue distilled under reduced pressure to give 6-(2-tetrahydropyranyloxy)hexanol (46.1 g., 57%), b.p. 102°–120°C./0.2 mm.Hg.

Pyridine-sulphur trioxide complex (17.1 g., 0.108 mole) in dimethylsulphoxide (90 ml.) was added dropwise to a mixture of 6-(2-tetrahydropyranyloxy)-hexanol (7.2 g., 0.036 mole) and triethylamine (27 g., 0.27 mole) in dimethylsulphoxide (90 ml.) at 25°C. The mixture was stirred for a further hour, then 2N acetic acid (100 ml.), water (200 ml.) and diethyl ether (500 ml.) added successively, the layers separated and the aqueous layer extracted with diethyl ether. The combined ether solutions were washed quickly with 2N hydrochloric acid, aqueous sodium carbonate and then water, and dried over sodium sulphate. The solvent was evaporated and the residue distilled under reduced pressure to give 6-(2-tetrahydropyranyloxy)hexanal (4.65 g., 63%), b.p. 75°–105°C./0.15 mm.Hg.

EXAMPLE 4

7-[2-Hydroxy-5-(4-ethyl-3-hydroxy-1-octenyl)cyclopentyl]-heptanoic acid i. Preparation of 2-(7-hydroxyheptyl)-3-(4-ethyl-3-oxo-1-octenyl)cyclopentanol A mixture of 3-hydroxy-2-(7-hydroxyheptyl)-cyclopentanecarbaldehyde (6 g.) [prepared as described in Example 1] and 2-ethylhexanoylmethylenetriphenylphosphorane (9g.) in dry tetrahydrofuran (70 ml.) was heated under reflux under nitrogen for 6 hours. The solvent was removed in vacuo and the residue was triturated with petrol (b.p. 40°–α°C.) with cooling to 0°C. and filtered to remove triphenylphosphine oxide. Evaporation of the filtrate then gave crude 2-(7-hydroxyheptyl)-3-(4-ethyl-3-oxo-1-octenyl)cyclopentanol (4.4 g.), $\nu_{max}$ 1620 cm$^{-1}$, 1655 cm$^{-1}$ (liquid film), which was used in the next step without further purification.

ii. Preparation of 7-[2-oxo-5-(4-ethyl-3-oco-1-octenyl)-cyclopentyl]-heptanoic acid 8N Jones' reagent (0.4 ml.) was added to a stirred solution of 2-(7-hydroxyheptyl)-3-(4-ethyl-3-oxo-1-octenyl)cyclopentanol (0.42 g.) in acetone (4 ml.) at below 20°C. at such a rate that the deep red coloration caused by the addition of one drop of reagent had changed to green before addition of the next drop. The reaction mixture was diluted with sufficient water to dissolve the precipitated chromium salts and then extracted three times with diethyl ether. The combined ether extracts were washed with 2N aqueous sulphuric acid and then added to 10% aqueous sodium carbonate (50 ml.) and stirred for 1 hour. The aqueous layer was separated and covered with a layer of diethyl ether and concentrated hydrochloric acid added dropwise until the pH was 1. The ether layer was separated and the aqueous layer again extracted with diethyl ether. The combined extracts were dried over magnesium sulphate and the ether was removed in vacuo to give 7-[2-oxo-5-(4-ethyl-3-oxo-1-octenyl)cyclopentyl]-heptanoic acid (0.12 g.), $\nu_{max}$ 1620 cm$^{-1}$, 1680 cm$^{-1}$, 1700 cm$^{-1}$ and 1730 cm$^{-1}$ (liquid film).

iii. Preparation of 7-[2-hydroxy-5-(4-ethyl-3-hydroxy-1-octenyl)cyclopentyl]heptanoic acid A solution of sodium borohydride (0.095 g.) in 0.2N aqueous sodium hydroxide (0.95 ml.) was added dropwise to a solution of 7-[2-oxo-5-(4-ethyl-3-oxo-1-octenyl)cyclopentyl]heptanoic acid (0.4 g.) in ethanol (9 ml.) and N aqueous sodium hydroxide (1.2 ml.). The resulting solution was stirred for 1 day, and then the ethanol was removed in vacuo. A small quantity of water was added, and the solution was extracted twice with diethyl ether (to remove non-acidic material). The aqueous solution was covered with a layer of diethyl ether and acidified to pH 1 by the dropwise addition of concentrated hydrochloric acid, cooling the solution to about 10°C. The ether layer was separated and the aqueous layer extracted twice more with diethyl ether. The combined ether extracts were dried over magnesium sulphate, evaporated and purified by preparative thin-layer chromatography to give 7[2-hydroxy-5-(4-ethyl-3-hydroxy-1-octenyl)cyclopentyl]heptanoic acid (60 mg.), $\nu_{max}$ 1700cm$^{-1}$, 980 cm$^{-1}$. (Found: C, 71.0; H, 10.4. $C_{22}H_{40}O_4$ requires C, 71.7; H, 10.9%).

The 2-ethylhexanoylmethylene triphenylphosphorane employed in this Example was prepared as follows:

2-Ethylhexanoyl chloride (60 g.) was added dropwise at <10°C. to a solution of diazomethane (20 g.) in diethyl ether (160 ml.) and the solution stirred overnight at ambient temperature. An excess of anhydrous hydrogen chloride was then bubbled into the solution (3/4 hour) and the mixture stirred for a further 1 hour. Crushed ice was added to give approximately 1 litre of aqueous solution. The aqueous layer was saturated with sodium chloride and the organic layer separated, washed with water and with aqueous sodium carbonate (twice) and again with water, and dried over magnesium sulphate. Evaporation gave crude 1-chloro-3-ethyl-2-heptanone (88.4 g.) which was used immediately in the next step.

A solution of 1-chloro-3-ethyl-2-heptanone (88.4 g.) and triphenylphosphine (81 g.) in chloroform (100 ml.) was saturated with nitrogen and refluxed under nitrogen overnight. The chloroform was removed in vacuo to give crude 2-oxo-3-ethylheptyltriphenylphosphonium chloride (176.1 g.).

Crude 2-oxo-3-ethylheptyltriphenylphosphonium chloride (88 g.) was added to a solution of sodium carbonate (100 g.) in water (1 litre) and the mixture stirred vigorously for 24 hours. The mixture was then extracted with diethyl ether and the extracts dried over magnesium sulphate. The solvent was evaporated and the crude product (63.3 g.) recrystallised from petrol (b.p. 60°–80°C.) to give 2-ethylhexanoylmethylenetriphenylphosphorane, m.p. 105.5°–107.5°C. (Found: C, 80.2; H, 7.5. $C_{27}H_{31}OP$ requires C, 80.5; H, 7.5%).

EXAMPLE 5

Methyl 7-[2-hydroxy-5-(3-hydroxy-1-octenyl)cyclopentyl]-heptanoate

A solution of diazomethane (0.327 g.) in dry diethyl ether (10 ml.) was added to a solution of 7-[2-hydroxy-5-(3-hydroxy-1-octenyl)cyclopentyl]heptanoic acid (0.4 g.) [prepared as described in Example 1] in dry diethyl ether (10 ml.). The resulting solution was allowed to stand at ambient temperature for 18 hours, during which time a solid precipitated. The solid was removed by filtration and the filtrate evaporated. The remaining traces of ether were removed from the residue by pumping under high vacuum to give methyl 7-[2-hydroxy-5-(3-hydroxy-1-octenyl)cyclopentyl]-heptanoate (0.3 g., 72%). (Found: C, 70.8; H, 10.6. $C_{21}H_{38}O_4$ requires C, 71.25; H, 10.72%) $\nu_{max}$1730 cm$^{-1}$, 980 cm$^{-1}$ (liquid film). N.M.R. (approximately 10% solution in deuterochloroform) 0.92δ (triplet J=5c/s, terminal CH$_3$) 1.7, 1.4δ (overlapping multiplets, cyclic and chain CH$_2$), 2.38δ (triplet J=6.5c/s, CH$_2$C—O), 2.70δ (broad singlet, —OH), 3.76δ (singlet —COOCH$_3$), 4.32, 4.15 and 4.00δ (overlapping multiplets, cis and trans

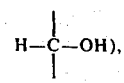

5.62δ (multiplet,

EXAMPLE 6

Methyl 7-[2-methoxy-5-(3-methoxy-1-octenyl)cyclopentyl]-heptanoate

A solution of methyl 7-[2-hydroxy-5-(3-hydroxy-1-octenyl)cyclopentyl]heptanoate (0.6 g.) [prepared as described in Example 5] in dry diethyl ether (30 ml.) was cooled to −40°C. Freshly prepared dry diazomethane in diethyl ether, cooled to −40°C., was added to the solution of methyl ester immediately after the addition of boron trifluoride dimethyl etherate (3 ml.). Diazomethane solution was added until the yellow colour persisted. After 15 minutes at −40°C. and standing at ambient temperature overnight the solution was filtered from precipitated polymethylenes, washed with sodium bicarbonate solution and water, dried over anhydrous sodium sulphate and evaporated in vacuo. The last traces of solvent were removed by pumping under high vacuum to give methyl 7-[2-methoxy-5-(3-methoxy-1-octenyl)cyclopentyl]heptanoate (0.42 g., 65%). (Found: C, 72.4; H, 10.3. $C_{23}H_{42}O_4$ requires C, 72.3; H,11.0%) $\nu_{max}$1730 cm$^{-1}$, 1100 cm$^{-1}$ and 990 cm$^{-1}$ (liquid film).

EXAMPLE 7

7-[2-Acetoxy-5-(3-acetoxy-1-octenyl)cyclopentyl]-heptanoic acid

To a solution of 7-[2-hydroxy-5-(3-hydroxy-1-octenyl)cyclcopentyl]heptanoic acid (0.5 g.) [prepared as described in Example 1] in dry pyridine (12.5 ml.) was added acetic anhydride (12.5 ml.). The resulting solution was allowed to stand at ambient temperature for 20 hours. This was then diluted with water under icebath cooling. This aqueous solution was extracted twice with diethyl ether and the combined extracts evaporated in vacuo to remove the excess acetic anhydride. The residue was taken up in diethyl ether washed with dilute hydrochloric acid and water, then dried over magnesium sulphate. Evaporation in vacuo gave 7-[2-acetoxy-5-(3-acetoxy-1-octenyl)cyclopentyl]heptanoic acid (0.4 g., 64%). (Found: C, 68.6; H, 9.6. $C_{24}H_{40}O_6$ requires C, 68,0; H, 9.4%) $\nu_{max}$1725 cm$^{-1}$, 1700 cm$^{-1}$, 1380 cm$^{-1}$, 1240 cm$^{-1}$ and 970 cm$^{-1}$ (liquid film). Thin layer chromatography 1 spot.

EXAMPLE 8

N-Methyl-7-[2-hydroxy-5-(3-hydroxy-1-octenyl)cyclopentyl]heptanoamide

To a solution of methyl 7-[2-hydroxy-5-(3-hydroxy-1-octenyl)cyclopentyl]heptanoate (0.8 g.) [prepared as described in Example 5] in ethanol (16 ml.) was added 33% methylamine in ethanol (4 ml.) followed by sodium ethoxide in ethanol [0.8 ml. of a solution prepared by dissolving sodium (0.2 g.) in ethanol (1 ml.)]. The resulting solution was refluxed for 1 day and the ethanol removed in vacuo. The residue was diluted with ice-cooled water and extracted twice with dichloromethane. The combined dichloromethane extracts were dried over magnesium sulphate and evaporated to give N-methyl-7-[2-hydroxy-5-(3-hydroxy-1-octenyl)-cyclopentyl]heptanoamide (0.2g., 25%). Found: C, 71.9; H, 10.6. $C_{21}H_{39}NO_3$ requires C, 71.4; H, 11.05%) $\nu_{max}$3300 cm$^{-1}$, 1650 cm$^{-1}$, 1570 cm$^{-1}$ and 980 cm$^{-1}$ (liquid film).

EXAMPLE 9

7-[2-Hydroxy-5-(3-hydroxy-1-octenyl)cyclopentyl]-heptanohydrazide

A solution of methyl 7-[2-hydroxy-5-(3-hydroxy-1-octenyl)cyclopentyl]heptanoate (0.4 g.), [prepared as described in Example 5], 100% hydrazine hydrate (0.8 ml.) and methanol (10 ml.) was refluxed for 24 hours. After 12 hours reflux a further amount of hydrazine hydrate (0.8 ml.) was added. The methanol was removed in vacuo and the residue diluted with water. The resulting solution was extracted twice with diethyl ether. The combined ether extracts were dried over magnesium sulphate to give 7-[2-hydroxy-5-(3-hydroxy-1-octenyl)-cyclopentyl]heptanohydrazide (0.25 g., 62.5%). (Found: C, 67.4; H, 10.6; N, 7.9. $C_{20}H_{38}N_2O_3$ requires C, 67.8; H,10.72; N, 7.9%) $\nu_{max}$3300 cm$^{-1}$, 1650 cm$^{-1}$ (shoulder 1630 cm$^{-1}$), 980 cm$^{-1}$ (liquid film).

EXAMPLE 10

7-[2-Hydroxy-5-(3-hydroxyoctyl)cyclopentyl]heptanoic acid

A solution of 7-[2-oxo-5-(3-oxo-1-octenyl)cyclopentyl]heptanoic acid (1.0 g.) [prepared as described in Example 1] in ethanol (50 ml.) was catalytically reduced with hydrogen and Raney nickel [Raney nickel (1 g.); hydrogen pressure 400 p.s.i.] which on evaporation gave 7-[2-oxo-5-(3-oxo-1-octyl)cyclopentyl]heptanoic acid (1.0 g.), $\nu_{max}$1720 cm$^{-1}$, 1700 cm$^{-1}$ (liquid film). N.M.R. (approximately 10% solution in deuterochloroform) 0.90 $\delta$ (triplet J=5c/s, terminal CH$_3$), 1.35 $\delta$ (series of multiplets, chain CH$_2$), 1.6 $\delta$ (multiplet, cyclic CH$_2$), 2.1–2.5 $\delta$ (series of multiplets, CH$_2$C=O), 10.23 $\delta$ (broad singlet, —COOH).

A solution of the crude 7-[2-oxo-5-(3-oxo-1-octyl)-cyclopentyl]heptanoic acid (0.8 g.) in ethanol (20 ml.) was neutralised by addition of 1N sodium hydroxide (2.40 ml.). The resulting solution was then treated with a solution of sodium borohydride (0.25g.) in 0.2 N sodium hydroxide (2.5 ml.) and stirred at ambient temperature for 1 day. The ethanol was then evaporated in vacuo, water added and any non-acidic material removed by extraction with diethyl ether. The aqueous phase was covered with a layer of diethyl ether and acidified by dropwise addition of hydrochloric acid. The ether layer was separated and the aqueous phase extracted again with diethyl ether. The combined ether extracts were dried over sodium sulphate and evaporated to give 7-[2-hydroxy-5-(3-hydroxy-1-octyl)cyclopentyl]heptanoic acid (0.6 g.).

A pure sample of the acid was achieved by separation using preparative thin layer chromatography. The plates were coated with silica gel and eluted with a mixture of benzene (30) : dioxane (9) : formic acid (1). (Found: C, 69.9; H, 11.0. $C_{20}H_{38}O_4$ requires C, 70.2; H, 11.1%), $\nu_{max}$1700 cm$^{-1}$ (liquid film). N.M.R. (approximately 10% solution in deuterochloroform) 0.94$\delta$ (triplet J=5c/s, terminal CH$_3$), 1.7, 1.4 $\delta$ (overlapping multiplets, cyclic and chain —CH$_2$), 2.38 $\delta$ (triplet J= 6.5c/s —CH$_2$C=O), 4.35, 4.04, 3.72 $\delta$ (overlapping mutiplets, cis and trans

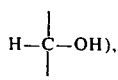

5.5δ (broad singlet —OH).

EXAMPLE 11

Methyl 7-[2-hydroxy-5-(3-hydroxy-1,2-epoxy-1-octyl)-cyclopentyl]heptanoate

A solution of methyl 7-[2-hydroxy-5-(3-hydroxy-1-octenyl)cyclopentyl]heptanoate (1.0 g.) [prepared as described in Example 5], metachlorperbenzoic acid (2.0 g.) and dichloromethane (30 ml.) was refluxed for 15 days. The precipitated metachlorbenzoic acid was filtered from the cooled solution and washed with dichloromethane. The filtrate was washed successively with sodium sulphite solution, twice with 5% sodium bicarbonate solution and finally water, dried over sodium sulphate and evaporated to give methyl 7-[2-hydroxy-5-(3-hydroxy-1,2-epoxy-1-octyl)cyclopentyl]heptanoate (0.96 g., 92%), $\nu_{max}$ 3450 cm$^{-1}$, 1730 cm$^{-1}$ and 1170 cm$^{-1}$.

EXAMPLE 12

Methyl 7-[2-hydroxy-5-(3-hydroxy-1,2-methylene-1-octyl)cyclopentyl]heptanoate

A suspension of zinc-copper couple (1.0 g.) (prepared by the method of R.S. Shank and H. Schechter, J. Org. Chem. (1959), 24, 1825) in diiodomethane (4.0 g.) and dry diethyl ether (10 ml.) was refluxed with a crystal of iodine for 0.5 hours. To the resulting suspension was added methyl 7-[2-hydroxy-5-(3-hydroxy-1-octenyl)cyclopentyl]heptanoate (1.0 g.) [prepared as described in Example 5] in dry diethyl ether (10 ml.) and the resulting mixture was refluxed for 24 hours. Addition of saturated ammonium chloride broke up the complex formed and the remaining zinc-copper couple was removed by filtration. The filtrate was separated and the diethyl ether layer dried over magnesium sulphate and evaporated to give methyl 7-[2-hydroxy-5-(3-hydroxy-1,2-methylene-1-octyl)cyclopentyl]heptanoate (1.04 g.). This was purified by preparative thin layer chromatography using the system employed in Example 10, $\nu_{max}$ 3400 cm$^{-1}$, 1730 cm$^{-1}$ and 1170 cm$^{-1}$.

EXAMPLE 13

Preparation of 7-[2-hydroxy-5-(4-ethyl-3-hydroxyoctyl)cyclopentyl]-heptanoic acid A stirred solution of 7-[2-hydroxy-5-(4-ethyl-3-hydroxyoct-1-enyl)-cyclopentyl]heptanoic acid [0.6 g; prepared as described in Example 4(iii)] in ethanol (25 ml.) was reduced with hydrogen at a hydrogen pressure of 6.3 kg./cm$^2$ and in the presence of a 5% palladium on charcoal catalyst (0.68 g.). The catalyst was then filtered off and the filtrate evaporated to give 7-[2-hydroxy-5-(4-ethyl-3-hydroxyoctyl)cyclopentyl]heptanoic acid (0.47 g.), $\nu_{max}$ 1700 cm$^{-1}$ (Found: C, 71.2; H, 11.7%; $C_{22}H_{42}O_4$ requires C, 71.4; H, 11.4%). N.M.R. (approximately 10% solution in deuterochloroform) 0.65–1.05δ (2 overlapping triplets, terminal CH$_3$ groups), 1.05–2.2δ (overlapping multiplets, cyclic and chain CH$_2$ groups), 2.30δ (triplet CH$_2$C=O), 3.60–3.88δ, 4.2δ (multiplets, methylidene groups attached to hydroxy groups), 5.6–6.6δ broad singlet, OH and COOH groups).

The present invention includes within its scope pharmaceutical compositions which comprise at least one compound of the abovementioned novel class of cyclopentane derivatives of general formula I or, when R$^4$ represents a carboxy group, non-toxic salts thereof, together with a pharmaceutical carrier or coating. In clinical practice the novel compounds of the present invention will normally be administered orally, rectally, vaginally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for rectal administration include suppositories formulated in manner known per se and containing one or more of the active compounds. Solid compositions for vaginal administration include pessaries or ovules formulated in manner known per se and containing one or more of the active compounds.

Preparations according to the invention for parenteral administration include sterile aqueous or nonaqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised, for example, by filtration through a bacteria-retaining filter by incorporation of sterilising agents in the compositions, by irradiation, or by heating. They may also be manufactured in the form of sterile solid compositions, which can be dissolved in sterile water or some other sterile injectable medium immediately before use.

The percentage of active ingredient in the compositions of the invention may be varied; in general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the adult, the doses are generally between 0.05 and 2 mg., preferably between 0.05 and 0.5 mg., by aerosol administration as bronchodilators, between 0.01 and 4.0 mg., preferably between 0.01 and 0.1 mg., per kilogram body weight by intravenous administration as bronchodilators, between 0.15 and 4.0 mg., preferably between 0.15 and 1.5 mg., per kilogram body weight by intravenous administration as hypotensives, between 0.001 and 0.15 mg., preferably between 0.001 and 0.01 mg., per kilogram body weight orally as inhibitors or gastric acid secretion and between 0.005 and 1.0 mg., preferably between 0.005 and 0.05 mg., per kilogram body weight by intravenous administration, more particularly by intravenous infusion at a rate of between 0.01 and 20µg., preferably between 0.01 and 0.1µg., per kilogram body weight/minute as stimulators of uterine contraction. If necessary these doses may be repeated as and when required.

The compounds of general formula I and, when $R^4$ represents a carboxy group, non-toxic salts thereof may be administered orally as bronchodilators by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely divided liquid particles suitable for inhalation. Advantageously, the solution to be nebulized is diluted and preferably aqueous, solutions containing from 0.5 to 20 mg., and preferably 0.5 to 5.0 mg., of active ingredient per ml. of solution being particularly suitable. The solutions may contain stabilizing agents such as sodium bisulphite and buffering agents to give it an isotonic character, e.g. sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active ingredients in pharmaceutically acceptable solvents, e.g. ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically acceptable volatile liquid propellants, in conventional pressurized packs which may be made of any suitable material e.g. metal, plastics or glass, adequate to withstand the pressures generated by the volatile propellant in the pack. Pressurized pharmaceutically acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 and 65 pounds, and more especially between about 30 and 55 pounds, per square inch gauge at 21°C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21°C.) and dichlorotetrafluoroethane (vapour pressure 28 pounds per square inch gauge at 21°C.) may be mixed in varying proportions to give propellants having vapour pressures intermediate between those of two constituents, e.g. a mixture of dichlorodifluoromethane and dichlorotetrafluoroethane in the proportions 38:62 respectively by weight has a vapour pressure of 53 pounds per square inch gauge at 21°C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 0.5 to 20 mg., and more particularly 0.5 to 5.0 mg., of active ingredient per ml. of solution or suspension. It is important that the pH of solutions and suspensions used, according to the present invention, to generate aerosols should be kept within the range 3 to 8 and preferable that they should be stored at or below 4°C., to avoid pharmacological deactivation of the active ingredient.

In carrying out the present invention, the means of producing an aerosol for inhalation should be selected in accordance with the physico-chemical properties of the active ingredient.

By the term "pharmaceutically acceptable" as applied in this specification to solvent, suspending or dispersing agents, propellants and gases is meant solvent, suspending or dispersing agents, propellants and gases which are non-toxic when used in aerosols suitable for inhalation therapy.

It is highly desirable that the aerosols should have a particle size less than about 10 microns and preferably less than 5 microns, for example between 0.5 and 3 microns, to ensure effective distribution to very narrow bronchioles. Preferably, administration is by means of devices enabling controlled quantities of the active ingredients to be administered, for example by means of the metered valves hereinbefore mentioned.

The following Examples illustrate pharmaceutical compositions according to the invention.

EXAMPLE 14

7-[2-Hydroxy-5-(4-ethyl-3-hydroxy-1-octenyl)cyclopentyl]heptanoic acid (300 mg.) was dissolved in ethanol (1 ml.) and the solution obtained was added to an aqueous solution (12 ml.) containing sodium carbonate (50 mg.). 0.9% w/v. Aqueous sodium chloride solution (2 ml.) was then added to give a final volume of 15 ml. The solution was then sterilised by passage through a bacteria-retaining filter and placed in 1.5 ml. portions in 5 ml. ampoules, to give 30 mg. of the heptanoic acid derivative (in the form of its sodium salt) per ampoule. The contents of the ampoules were freeze-dried and the ampoules sealed. Dissolution of the contents of an ampoule in a suitable volume, e.g. 2 ml., of sterile water or physiological saline gave a solution ready for administration by injection.

EXAMPLE 15

7-[2-Hydroxy-5-(4-ethyl-3-hydroxyoctyl)cyclopentyl]heptanoic acid (300 mg.) was dissolved in ethanol (1 ml.) and the solution obtained was added to an aqueous solution (12 ml.) containing sodium carbonate (50 mg.). Aqueous sodium chloride solution (2 ml; 0.9% w/v) was then added to give a final volume of 15 ml. The solution was then sterilised by passage through a bacteria-retaining filter and placed in 1.5 ml. portions in 5 ml. ampoules, to give 30 mg. of the heptanoic acid derivative (in the form of its sodium salt) per ampoule. The contents of the ampoules were freeze-dried and the ampoules sealed. Dissolution of the contents of an ampoule in a suitable volume, e.g. 2 ml., of sterile water of physiological saline gave a solution ready for administration by injection.

We claim:

1. A cyclopentane compound of the formula:

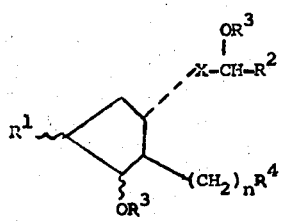

wherein $R^1$ represents a hydrogen atom or a lower alkyl group, $R^2$ represents a straight- or branched-chain alkyl group of 1 to 10 carbon atoms, $R^3$ represents a hydrogen atom or a lower alkyl, lower alkenyl, phenyl-(lower)alkyl and lower alkanoyl group, $R^4$ represents a group of formula:

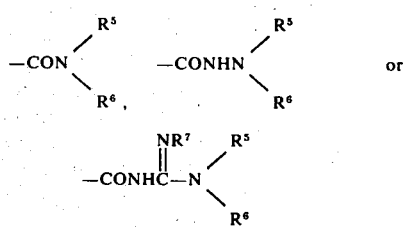

wherein $R^5$, $R^6$ and $R^7$ each represents a hydrogen atom or a lower alkyl group, X represents a vinylene, ethylene, or cyclopropylene group, and $n$ represents 5, 6, 7 or 8.

2. N-Methyl-7-[2-hydroxy-5-(3-hydroxy-1-octenyl)-cyclopentyl]-heptanoamide.

3. 7-[2-Hydroxy-5-(3-hydroxy-1-octenyl)cyclopentyl]heptanohydrazide.

* * * * *